United States Patent
Stoffaneller et al.

(10) Patent No.: US 8,687,831 B2
(45) Date of Patent: Apr. 1, 2014

(54) OPTIMIZED ENERGY AND DATA TRANSFER IN HEARING IMPLANT SYSTEMS

(71) Applicant: MED-EL Elektromedizinische Geraete GmbH, Innsbruck (AT)

(72) Inventors: Martin Stoffaneller, Innsbruck (AT); Peter Schleich, Telfs (AT); Thomas Schwarzenbeck, Innsbruck (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/661,232

(22) Filed: Oct. 26, 2012

(65) Prior Publication Data
US 2013/0108091 A1 May 2, 2013

Related U.S. Application Data

(60) Provisional application No. 61/552,036, filed on Oct. 27, 2011.

(51) Int. Cl.
*H04R 25/00* (2006.01)
*G10L 21/00* (2013.01)

(52) U.S. Cl.
USPC ............ 381/315; 704/210; 704/214; 704/215

(58) Field of Classification Search
USPC ................. 381/312, 315; 600/25; 607/55, 57; 704/210, 214, 215, 240
See application file for complete search history.

(56) References Cited

U.S. PATENT DOCUMENTS

| | | | |
|---|---|---|---|
| 2011/0038489 A1* | 2/2011 | Visser et al. | 381/92 |
| 2013/0165992 A1* | 6/2013 | Swanson | 607/57 |

* cited by examiner

*Primary Examiner* — Brian Ensey
*Assistant Examiner* — Norman Yu
(74) *Attorney, Agent, or Firm* — Sunstein Kann Murphy & Timbers LLP

(57) ABSTRACT

An external device for a hearing implant system and a hearing implant system having an external device is described. An external transmitter generates a radio-frequency inductive link signal to an implanted receiver including a sequence of data word segments which communicate data to the implanted receiver, and a sequence of data word pause segments between each data word segment which communicate energy without data to the implanted receiver. A data word pause controller controls the inductive link signal during the data word pause segments according to an energy management rule.

14 Claims, 4 Drawing Sheets

OPTIMIZED ENERGY AND DATA TRANSFER IN HEARING IMPLANT SYSTEMS

This application claims priority from U.S. Provisional Patent Application 61/552,036, filed Oct. 27, 2011, which is incorporated herein by reference.

FIELD OF THE INVENTION

The present invention relates to cochlear implant systems, and more specifically to power management in such systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processor 111 which implements one of various known signal processing schemes. The processed signal is converted by the external signal processor 111 into a digital data format, such as a sequence of data frames, for transmission into a receiver processor in a stimulator processor 108. Besides extracting the audio information, the receiver processor in the stimulator processor 108 may perform additional signal processing such as error correction, pulse formation, etc., and produces a stimulation pattern (based on the extracted audio information) that is sent through connected wires 109 to an implant electrode 110. Typically, the implant electrode 110 includes multiple electrodes on its surface that provide selective stimulation of the cochlea 104.

The stimulator processor 108 typically does not have an internal battery so the radio-frequency inductive link signal from the external signal processor 111 is used both for transferring data (for example, for stimulation) and also to provide energy for powering the implanted components. This raises a number of technical challenges. The transmission of energy to the implanted components should be power efficient and independent of data transmission without impairing the overall system performance. In addition, the implant supply voltage is affected by many factors such as electrode load impedance, inductive link coil coupling distance, number of stimulated channels, stimulation amplitude, and stimulation duration. Notwithstanding these many factors, the implant supply voltage should be as stable as possible to generate reproducible stimulation pulses. The implant supply voltage also needs to exceed a predefined minimal supply voltage $V_{THR}$ for some minimal defined initialization period. The stimulator processor 108 also must scan the inductive link signal for data words and decode those correctly. These considerations vie with the need for low power consumption since the implant supply voltage is not needed when no stimulation is produced and energy losses increase (at least linearly) with the supply voltage.

In general, a stable voltage supply is achieved by voltage regulation, which can be realized by feedback from within the implant (regulator with internal feedback) or by telemetry of the supply voltage status to the external components which regulate the internal supply voltage from outside (regulator with external feedback). See, e.g. Mark van Paemel, *High-Efficiency Transmission for Medical Implants*, IEEE Solid-State Circuits Magazine, Digital Object Identifier 10.1109/MSSC.2010.939572; incorporated herein by reference. One disadvantage of these regulation schemes is the additional circuitry that decreases the overall circuit reliability and which itself consumes energy. For example, the simplest but very energy inefficient regulator is a Zener-diode.

As mentioned the stimulator processor 108 typically is not equipped with batteries but instead uses load capacitors for energy storage. This means that the implant cannot store large amounts of energy and so any excess transferred energy will be wasted. Typically the inductive link signal uses a Manchester coded ASK (Amplitude Shift Keying) signal, which ensures that both data and energy are continuously transferred to the stimulator processor 108 whenever data needs to be delivered. When no acoustic information needs to be transferred, redundant Manchester coded data can be sent. For example, logical 1's or 0's are represented in a sequence of $[RF_{off}/RF_{on}]$ or $[RF_{on}/RF_{off}]$ respectively. Sending redundant Manchester coded data is relatively easy to implement, but that brings the disadvantage that the same amount of energy is transferred to the stimulator processor 108 and surrounding tissue even though less energy is needed since no data is transferred and hence less power is consumed.

SUMMARY OF THE INVENTION

Embodiments of the present invention are directed to an hearing implant system comprising an implantable device arrangement and external device arrangement, and an external device arrangement for a hearing implant system. An external transmitter generates a radio-frequency inductive link signal to an implanted receiver including a sequence of data word segments which communicate data to the implanted receiver, and a sequence of data word pause segments between each data word segment which communicate energy without data to the implanted receiver. A data word pause controller controls the inductive link signal during the data word pause segments according to an energy management rule.

The energy management rule may include maintaining a supply voltage within the implanted receiver above a minimum supply voltage level, reaching a desired supply voltage level within the implanted receiver before the beginning of each data word segment, and/or a probability of a next data word segment occurring in a non-deterministic data processing system.

The data word pause controller may control a duty cycle of a gating signal for the inductive link signal according to the energy management rule. For example, a plurality of different gating signal duty cycles may be used which steadily increase during the data word pause segments. In addition or alternatively, the data word pause controller may control the inductive link signal to be OFF for a period immediately following each data word segment, and ON for a period immediately before each data word segment.

DETAILED DESCRIPTION OF SPECIFIC EMBODIMENTS

Figure 1:
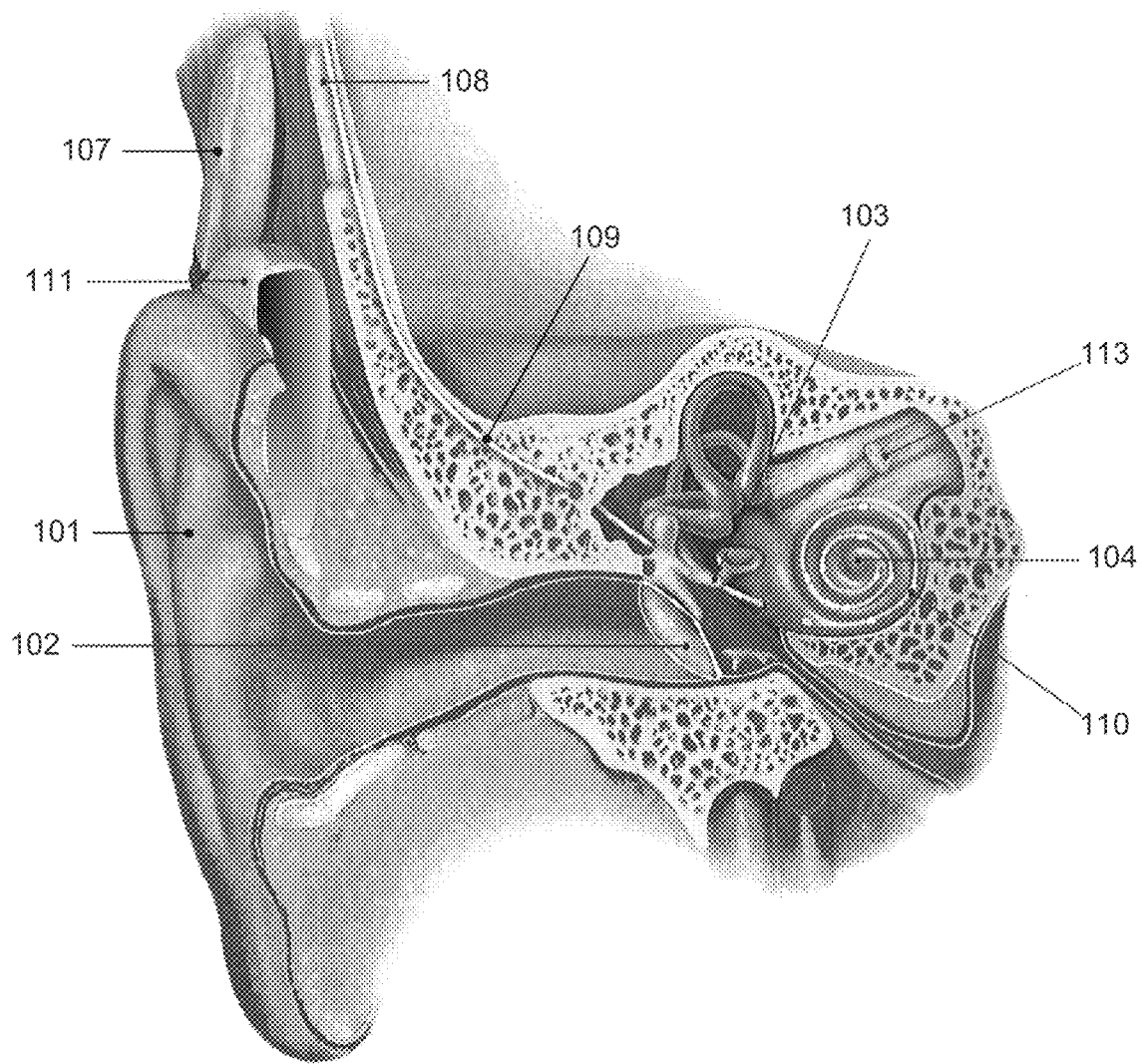
FIG. 1 shows anatomical features of a typical human ear having a cochlear implant system.
Figures 2, 3:
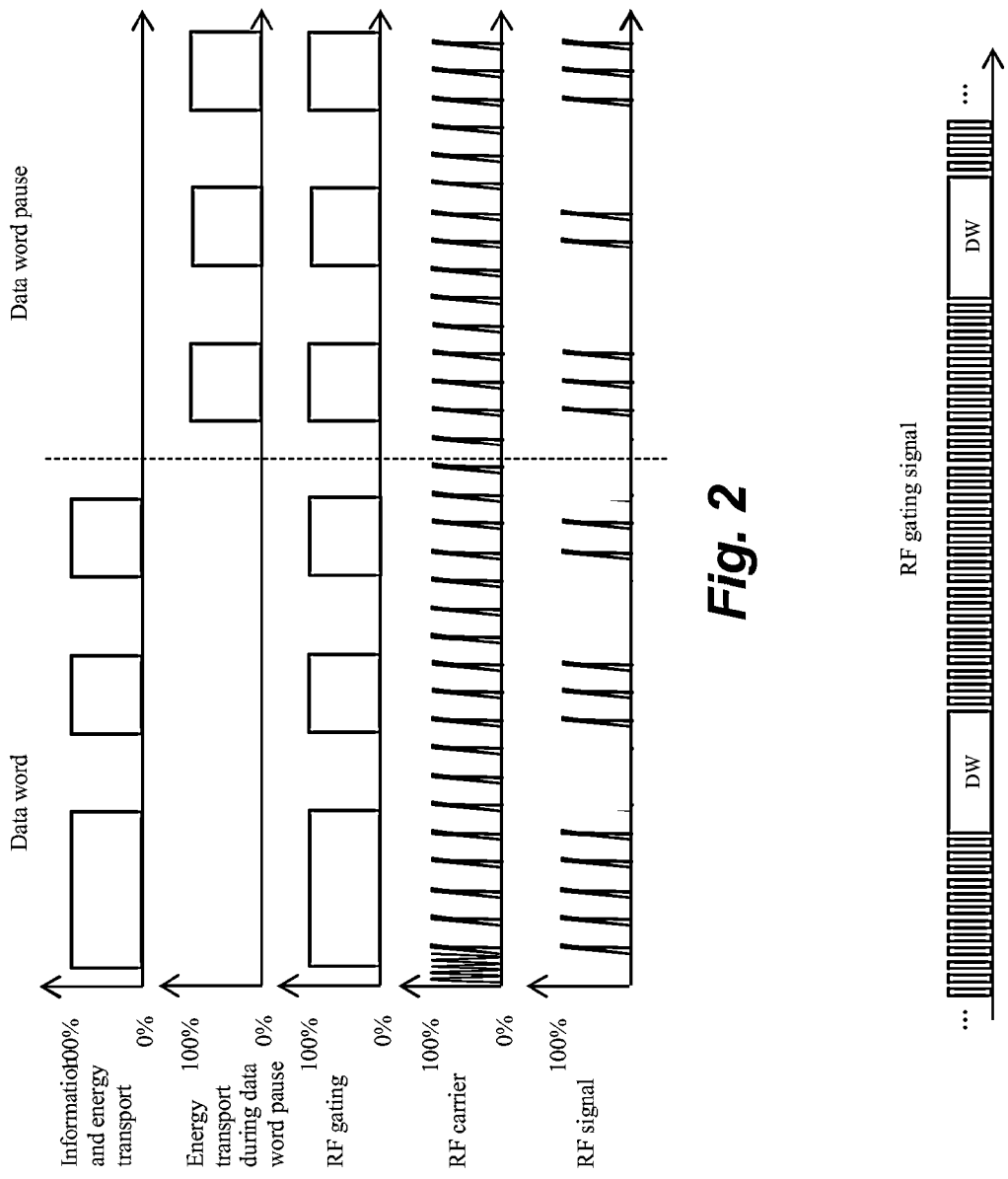
FIG. 2 shows two phases of the inductive link signal in a hearing implant system.
FIG. 3 shows a prior art data word and data word pause sequence.

Looking more closely at the inductive link signal in a hearing implant system, the top waveform in FIG. 2 shows two different phases of that signal, with the left side containing data word segments and the right side being a data word pause segment. Data word segments are delivered by an rf carrier signal to the implanted components and include information about the stimulation amplitude and electrode address, stimulus form, stimulation mode, etc. No information can be delivered during the data word pause segment, though the rf carrier signal is available to deliver energy to the implanted components.

The stimulation strategies for hearing implants is typically deterministic in the sense that the stimulation is repeated in a well-defined periodical pattern, preferably using high stimulation rates (e.g. Continuous Interleaved Stimulation, CIS). This means that the data words occur regularly and repeatedly so that continuous energy transfer by the data words to the implant is guaranteed. But data word pause segments also are desirable because for deterministic stimulation strategies, the stimulation pulse frequency (and so the data word frequency) strongly correlates with speech perception. In addition, the data word decoding circuitry also must be able to handle signals containing no data word without resulting in an error.

If these prerequisites are fulfilled the data word pause segments can be filled up with rf carrier signals without data. Thus embodiments of the present invention control the timing of energy delivery to the implanted components during data word pause segments. For example, the second row in FIG. 2 shows three pulse periods during the data word pause segment during which the rf carrier may be used to deliver energy to the implanted components. During actual system operation, the data word segments and the data word pause segments in effect are concatenated as shown in the third row of FIG. 2, with the pulse periods representing times during which the rf carrier signal (fourth row of FIG. 2) is gated on. The result would then be an irregular sequence of rf carrier pulses as shown in the fifth row of FIG. 2 that is suitable for transmission by the inductive link and which provides both correct stimulation information and also energy for the implant without evoking a data word decoding error.

FIG. 3 shows a prior art data word and data word pause sequence where the rf carrier signal during the data word pause segment is a pulse train with a 50% duty cycle. Such an arrangement provides some level of energy transport to the implant during the data word pause segment signal but does not utilize an energy management rule that reflects current energy needs of the implanted receiver. By contrast, embodiments of the present invention do use an energy management rule that reflects current energy needs of the implanted receiver to control the rf carrier and energy transport over the inductive link during the data word pause segment.

Figure 4:
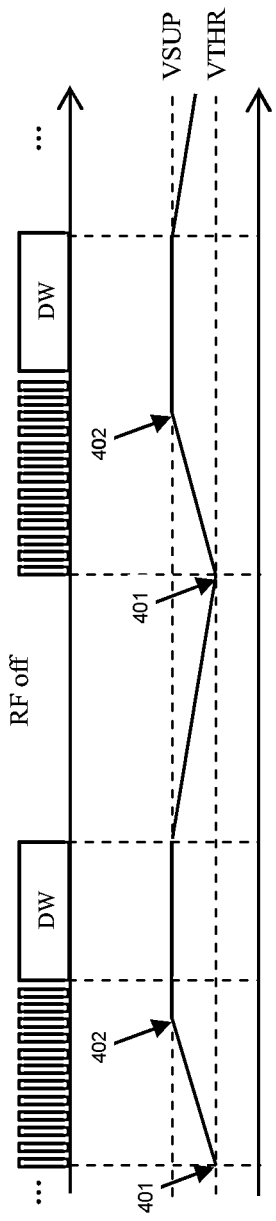
FIG. 4 shows a data word pause arrangement according to one embodiment of the present invention.

FIG. 4 shows an inductive link signal in one specific embodiment using such an energy management rule where the energy transport during the data word pause segment is based on a 50% duty cycle rf carrier pulse train that is switched on at some given instant within the data word pause segment, in this case, in the middle of the data word pause. Here the management rule might be that energy transfer is controlled to an amount that restores the supply voltage to a defined value needed for stimulation by the start of the next data word segment. However, as seen in the lower waveform in FIG. 4, there will be a significant supply voltage ripple as shown between the nominal supply voltage $V_{SUP}$ 402 and the threshold voltage level $V_{THR}$ 401. Such supply voltage ripple is undesirable due to the risk of undervoltage at the threshold voltage level $V_{THR}$ 401 and the energy losses when the supply voltage regulator operates at the nominal supply voltage $V_{SUP}$ 402.

Figure 5:
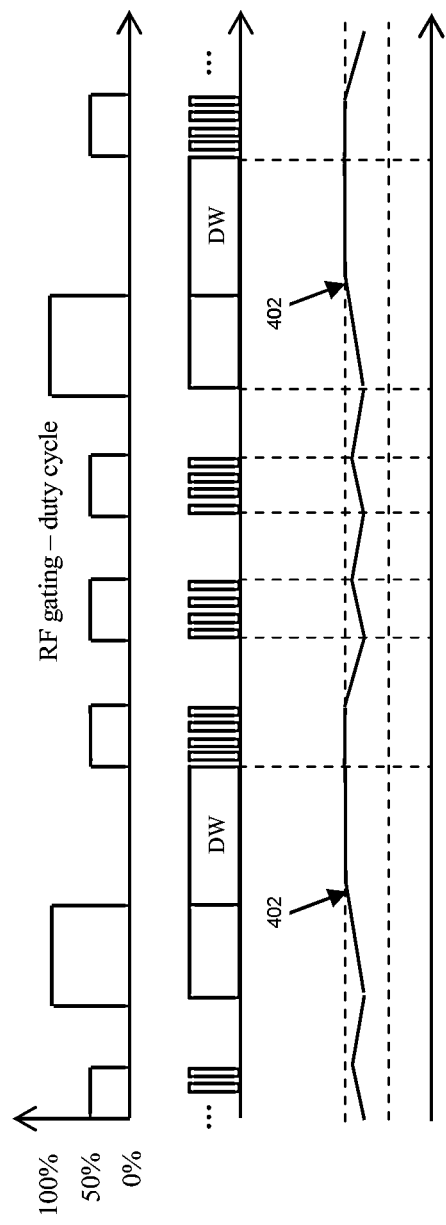
FIG. 5 shows a data word pause arrangement according to another embodiment of the present invention.

FIG. 5 shows an inductive link signal from another embodiment transferring energy during the data word pause according to an energy management rule which better reduced the supply voltage ripple by a periodically gating the rf carrier during the data word pause. Besides periodic gating of the rf carrier during the data word pause segment, supply voltage ripple and energy transport may also be improved by increasing the duty cycle of the rf carrier signal during the data word pause. Thus the inductive link signal in FIG. 5 also boosts energy and supply voltage within the implant by providing an rf carrier duty cycle of 100% (rf carrier is continuously on) just before the data word segment begins.

Figure 6:
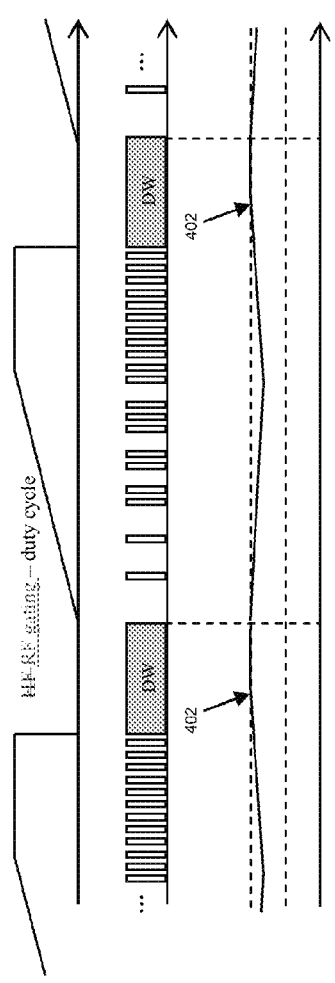
FIG. 6 shows a data word pause arrangement according to another embodiment of the present invention.
Figure 7:
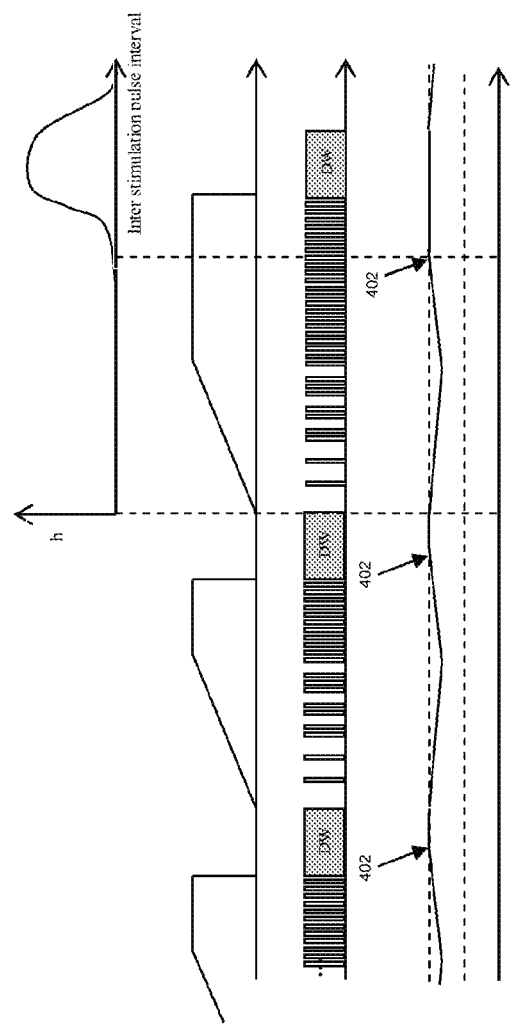
FIG. 7 shows a data word pause arrangement according to another embodiment of the present invention.

FIG. 6 shows another type of energy management rule which steadily increases the duty cycle of the rf carrier during the data word pause segment. Such an arrangement may also be useful for systems using a non-deterministic stimulation strategy where the data word segments do not recur in a well-defined regular repeated periodic pattern. For such applications, the energy management rule could be to gate the rf carrier signal based on a worst case estimate so that long inter-stimulation pulse intervals the load capacitor remains armed with energy for a longer time. FIG. 7 includes with the inductive link signal a histogram showing the probability for the duration of the inter stimulation pulse interval (i.e., the data word pause segment).

The energy management rule can be implemented by a pause controller, for example in the external signal processor 111, which controls energy transport by the inductive link during the data word pause segment. In specific embodiments, the pause controller may be implemented as a calculator within the external signal processor 111 that calculates the assumed energy dissipation per pulse and sends (at least) this the energy equivalent via the inductive link signal to the implanted components. A lookup table may be used with pre-calculated values that assigns to all stimulation pulses a corresponding data word pause signal energy transport value. This may reflect a worst case estimate that covers all possible stimulation pulses so that the energy provided by the inductive link signal during the data word pause segment at least covers the amount of energy that could be consumed by the implanted components within that stimulation setting for a patient at the most energy consuming fitting settings (e.g., the setting that is selected for MCL (Most Comfortable Loudness Level at all channels).

In addition or alternatively, the energy management rule may be based on one or more telemetry measurements from the implanted components. For example, a telemetry measurement may be performed when the implant is first initialized to determine system load requirements. Telemetry measurements may read the supply voltage for at least one load condition—for example, at a stimulation current source that is loaded by a resistor within the implant—to provide calibration data for energy consumption of the implant at the defined operational condition. This energy consumption calibration measurement(s) can provide a base for processing the timing of the energy management rule.

The total energy consumption of the whole system could be drastically reduced since energy inefficiency is cancelled out for times where the energy management rule has the rf carrier signal inactive. In addition, the implanted load capacitor could be selected for a smaller capacitance value and so have a smaller physical size and/or higher rated voltages at same size, thereby resulting in better long term reliability. And not only is there less power dissipation, but also the specific absorption rate (SAR) originating from the inductive link is minimized. (Note: even though there are presently no known contra-indications for electromagnetic fields, lower SARs still are desirable as with cellular phone standards). Lower power dissipation within the implant also reduces thermal heating and so in general extends the lifetime of the implanted components.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. An external device for a hearing implant system comprising: an external transmitter for generating a radio-frequency inductive link signal to an implanted receiver, the inductive link signal including: i. a sequence of data word segments which communicate data to the implanted receiver, and ii. a sequence of data word pause segments between each data word segment which communicate energy without data to the implanted receiver; and a data word pause controller for controlling the inductive link signal during the data word pause segments according to an energy management rule reflecting current energy needs of the implanted receiver; wherein the energy management rule includes maintaining a supply voltage within the implanted receiver above a minimum supply voltage level.

2. An external device according to claim 1, wherein the energy management rule further includes reaching a desired supply voltage level within the implanted receiver before the beginning of each data word segment.

3. An external device according to claim 1, wherein the energy management rule reflects a probability of a next data word segment occurring in a non-deterministic data processing system.

4. An external device according to claim 1, wherein the data word pause controller controls a duty cycle of a gating signal for the inductive link signal according to the energy management rule.

5. An external device according to claim 4, wherein the data word pause controller uses a plurality of different gating signal duty cycles.

6. An external device according to claim 5, wherein the gating signal duty cycles steadily increase during the data word pause segments.

7. An external device according to claim 1, wherein the data word pause controller controls the inductive link signal to be:
   i. OFF for a period immediately following each data word segment, and
   ii. ON for a period immediately before each data word segment.

8. A method for operating an external device in a hearing implant system comprising: generating a radio-frequency inductive link signal to an implanted receiver, the inductive link signal including: i. a sequence of data word segments which communicate data to the implanted receiver, and ii. a sequence of data word pause segments between each data word segment which communicate energy without data to the implanted receiver; and controlling the inductive link signal during the data word pause segments according to an energy management rule; wherein the energy management rule includes maintaining a supply voltage within the implanted receiver above a minimum supply voltage level.

9. A method according to claim 8, wherein the energy management rule further includes reaching a desired supply voltage level within the implanted receiver before the beginning of each data word segment.

10. A method according to claim 8, wherein the energy management reflects a probability of a next data word segment occurring in a non-deterministic data processing system.

11. A method according to claim 8, wherein controlling the inductive link signal includes controlling a duty cycle of a gating signal for the inductive link signal.

12. A method according to claim 11, wherein controlling the inductive link signal includes using a plurality of different gating signal duty cycles.

13. A method according to claim 12, wherein the gating signal duty cycles steadily increase during the data word pause segments.

14. A method according to claim 8, wherein controlling the inductive link signal includes controlling the inductive link signal to be:
   i. OFF for a period immediately following each data word segment, and
   ii. ON for a period immediately before each data word segment.

* * * * *